US006643005B1

(12) United States Patent
Hale et al.

(10) Patent No.: US 6,643,005 B1
(45) Date of Patent: Nov. 4, 2003

(54) LINE SENSING DEVICE FOR ULTRAFAST LASER ACOUSTIC INSPECTION USING ADAPTIVE OPTICS

(75) Inventors: Thomas C. Hale, Santa Fe, NM (US); David S. Moore, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 92 days.

(21) Appl. No.: 10/096,166

(22) Filed: Mar. 12, 2002

(51) Int. Cl.[7] .............................................. G01N 21/00
(52) U.S. Cl. ..................... 356/237.1; 356/630
(58) Field of Search .............................. 356/237.1, 503, 356/630

(56) References Cited

U.S. PATENT DOCUMENTS

| 5,748,317 | A | * | 5/1998 | Maris et al. | 356/502 |
|---|---|---|---|---|---|
| 6,069,703 | A | * | 5/2000 | Banet et al. | 356/630 |
| 6,115,127 | A | * | 9/2000 | Brodeur et al. | 356/503 |
| 6,134,006 | A | | 10/2000 | Telschow et al. | 356/357 |
| 6,401,540 | B1 | * | 6/2002 | Deason et al. | 73/657 |
| 6,552,803 | B1 | * | 4/2003 | Wang et al. | 356/503 |
| 2003/0020929 | A1 | * | 1/2003 | Morath et al. | 356/630 |

OTHER PUBLICATIONS

Grahn et al., "Picosecond Ultrasonics," IEEE Journal of Quantum Electronics, vol. 25, No. 12, pp. 2562–2569, Dec. 1989.

Maris, "Picosecond Ultrasonics," Scientific American, pp. 86–89, Jan. 1998.

Bonello et al., "Application of the Picosecond Ultrasonic Technique to the Study of Elastic and Time–resolved Thermal Properties of Materials," Ultrasonics, 35, pp. 223–231, 1997.

Perrin et al., "Interferometric Detection in Picosecond Ultrasonics," Physica B, 263–264, pp. 571–573, 1999.

* cited by examiner

*Primary Examiner*—Zandra V. Smith
*Assistant Examiner*—Kara Geisel
(74) *Attorney, Agent, or Firm*—Milton D. Wyrick

(57) ABSTRACT

Apparatus and method for inspecting thin film specimens along a line. A laser emits pulses of light that are split into first, second, third and fourth portions. A delay is introduced into the first portion of pulses and the first portion of pulses is directed onto a thin film specimen along a line. The third portion of pulses is directed onto the thin film specimen along the line. A delay is introduced into the fourth portion of pulses and the delayed fourth portion of pulses are directed to a photorefractive crystal. Pulses of light reflected from the thin film specimen are directed to the photorefractive crystal. Light from the photorefractive crystal is collected and transmitted to a linear photodiode array allowing inspection of the thin film specimens along a line.

5 Claims, 2 Drawing Sheets

$I_{AG}$ • acoustic generation beam
$I_S$ • signal beam
$I_{TS}$ • transmitted signal beam
$I_{DS}$ • duplicate signal beam
$I_R$ • reference beam

CONVENTIONAL

ADAPTIVE

LINE SENSING DEVICE FOR ULTRAFAST LASER ACOUSTIC INSPECTION USING ADAPTIVE OPTICS

The present invention generally relates to inspection of manufactured articles, and, more particularly, to laser acoustic inspection devices. This invention was made with Government support under Contract No. W-7405-ENG36 awarded by the U.S. Department of Energy. The Government has certain rights in the invention.

BACKGROUND OF THE INVENTION

The use of integrated circuits (ICs) during the last few decades is nothing short of fantastic. These miniature ICs are now used in a multitude of devices ranging from computers to toasters. These devices are typically constructed of a silicon wafer with impurities that create transistors precisely placed on the wafer. An arrangement of metal and insulating layers overlies the wafer for electrically connecting the transistors to one another. The overlying layers are typically between 50 angstroms and a few microns thick. The thickness and uniformity of the layers determine the efficiency of the chip and the application to which it is applied.

The manufacture of chips, although requiring the utmost in cleanliness and precision, has been refined to produce millions of devices in a short period of time. However, a continuing concern is producing efficacious devices that operate properly. As stated, one indication of proper operation is the thickness of the various semiconductor layers of the device. However, providing accurate measurement of the thickness is extremely difficult.

One efficient method is destructive as a chip is cut and viewed from the cut side. It is common for a manufacturer to try to control layer thickness by closely controlling every element affecting manufacture of the chips, such as pressure, temperature and humidity, and by destroying a few chips to verify the thickness of their layers.

Another fairly recently developed technique for chip layer thickness determination involves the use of laser beams to first excite a sample chip with a first optical pulse and then monitor the subsequent relaxation process with a weaker second optical pulse. However, this process can acoustically examine only a single point at a time. Because of this, chip inspection can be a lengthy operation, often causing delays in the production line. A need exists for equipment that can more quickly and accurately determine chip layer thickness.

It is therefore an object of the present invention to provide method and apparatus for efficiently determining the thickness of thin layers of a material.

It is another object of the present invention to provide method and apparatus capable of determining thickness of a thin layer of material along a line.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, a line sensing device for laser acoustic inspection of thin film specimens comprises a laser emitting pulses of light with a first beamsplitter outputting a first portion of the pulses of light and a second portion of the pulses of light. A second beamsplitter receives the second portion of the pulses of light and outputs a third portion of the pulses of light and a fourth portion of the pulses of light. A first optical delay line receives the first portion of the pulses of light for introducing a predetermined time delay into the first portion of the pulses of light. A second cylindrical lens receives the delayed first portion of the pulses of light and directs the delayed first portion of the pulses of light onto a thin film specimen along a line. A first cylindrical lens receives the third portion of the pulses of light for directing the third portion of the pulses of light onto the thin film specimen so that the third portion of the pulses of light contact the thin film specimen along the line. A second optical delay line receives the fourth portion of the pulses of light for introducing a predetermined time delay into the fourth portion of the pulses of light and directs the delayed fourth portion of the pulses of light to a photorefractive crystal. A third cylindrical lens receives reflected pulses of light from the thin film specimen and directs the reflected pulses of light to the photorefractive crystal. A fourth cylindrical lens collects light from the photorefractive crystal and transmits the collected light from the photorefractive crystal to a linear photodiode array allowing inspection of the thin film specimen along a line.

In another aspect of the present invention, and in accordance with its principles and purposes, a method of sensing a line along a thin film specimen comprises the steps of emitting ultrafast laser pulses; splitting the ultrafast laser pulses into a first portion, a second portion, a third portion and a fourth portion of the ultrafast laser pulses; delaying the first portion of the ultrafast laser pulses by a first predetermined period of time; directing the delayed first portion of the ultrafast laser pulses at the thin film specimen along a line; delaying the fourth portion of the ultrafast laser pulses by a second predetermined period of time; directing said delayed fourth portion of said ultrafast laser pulses to a photorefractive crystal; collecting pulses of light reflected from the thin film specimen and directing the reflected pulses of light to the photorefractive crystal; and collecting light from the photorefractive crystal and transmitting the collected light to a linear photodiode array allowing inspection of the thin film specimen along a line.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

The present invention provides method and apparatus for precise line measurement of layers of a semiconductor chip. The invention can be most easily understood through reference to the drawings.

Figure 1:
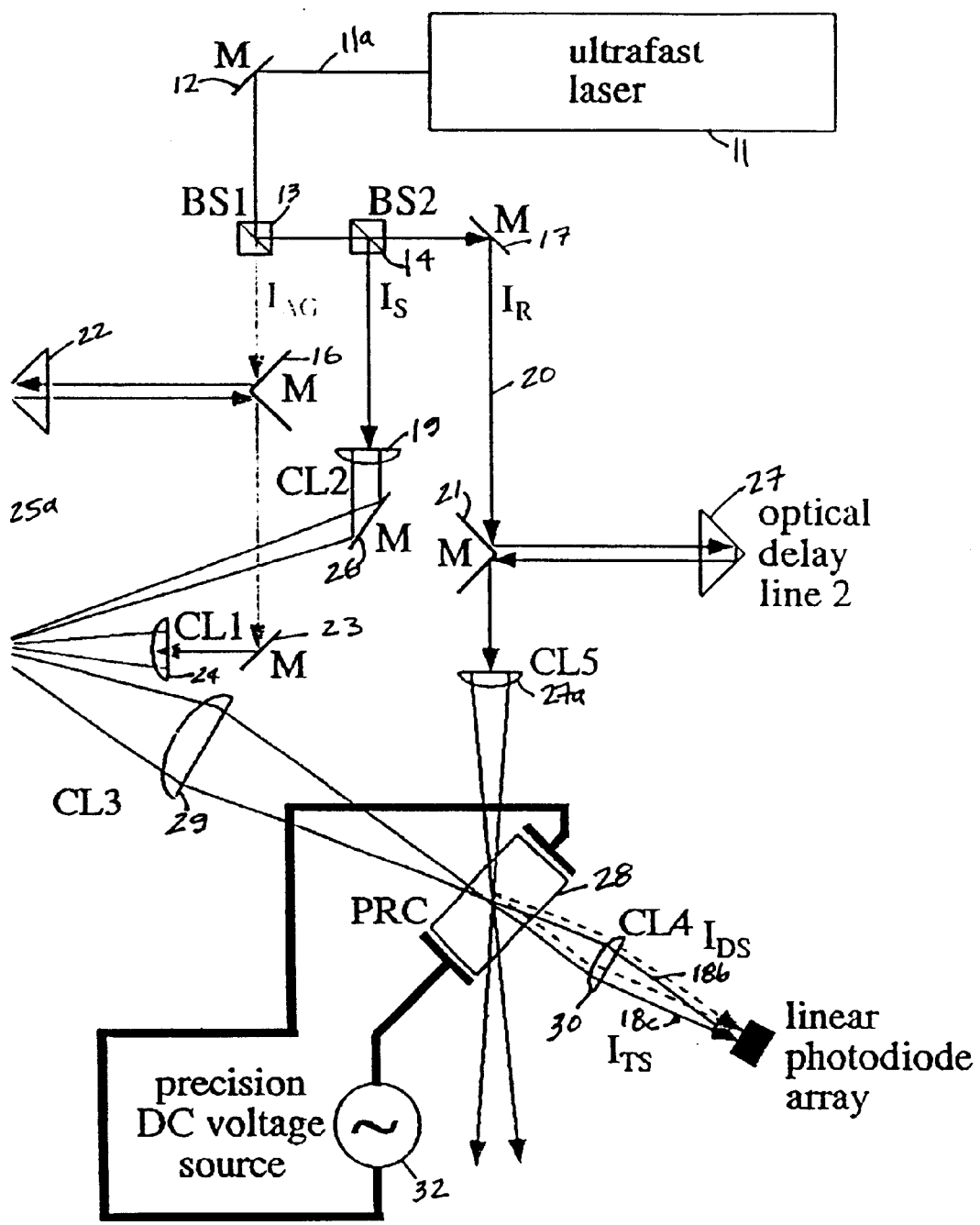
FIG. 1 is a optical schematic of one embodiment of the present invention.

Referring first to FIG. 1, there can be seen an optical schematic of one embodiment of the present invention. As seen, laser 11 emits main beam 11a, which is an ultrafast beam, having pulses of approximately 150 femtosecond duration and a repetition rate of up to 80 MHz. Laser 11 may be a titanium/sapphire (Ti/S) femtosecond laser. In this embodiment, main beam 11a is output to mirror 12 which redirects main beam 11a to beamsplitter 13. Beamsplitter 13 directs a portion of main beam 11a to beamsplitter 14 and directs acoustic generation beam 15 to mirror 16. Beamsplitter 14 then directs main beam 11a to mirror 17 and directs signal beam 18 to cylindrical lens 19. Mirror 17 reflects reference beam 20 to mirror 21.

Mirror 16 reflects acoustic generation beam 15 to optical delay line 22, which introduces a variable delay into acoustic generation beam 15 before returning it to mirror 16. Mirror 16 reflects the delayed acoustic generation beam to mirror 23, which reflects acoustic generation beam 15 through cylindrical lens 24 and onto thin film specimen 25 in the form of a line along thin film specimen 25. Cylindrical lens 19 focuses signal beam 18 into a line and directs it to mirror 26 where it is directed to thin film specimen 25.

Mirror 21 reflects reference beam 20 to optical delay line 27 where a variable delay (which delay can be introduced manually if desired) is introduced into reference beam 20 before it is returned to mirror 21 and reflected through cylindrical lens 27a to focus in photorefractive crystal 28. Additionally, light reflected from thin film specimen 25 is collected by cylindrical lens 29 and focused on photorefractive crystal 28, where it interacts with delayed reference beam 20 and the resulting output of photorefractive crystal 28 passes through cylindrical lens 30 to linear photodiode array 31. Photorefractive crystal 28 is biased by precision direct current (dc) voltage source 32.

The effect of short duration and high intensity acoustic generation beam 15 on thin film specimen 25 is to generate a thermoelastic mechanical perturbation, or acoustic wave, in thin film specimen 25 that travels inward. Since cylindrical lens 24 projects a line-shaped optical pulse onto thin film specimen 25, a line-shaped acoustic wave is generated. Acoustic mismatch between various layers within thin film specimen 25 causes part or all of the incoming picosecond acoustic wave generated in thin film 25a to be reflected back toward the surface of thin film specimen 25. The time-of-flight of the acoustic wavefront line reflection at different points across thin film specimen 25 is used to determine the thickness profile of top layer 25a.

Upon arrival at the surface of top layer 25a of thin film specimen 25, the reflected acoustic wave mechanically displaces the surface of top layer 25a, thereby modulating the phase of the incoming signal beam 18, which also is line shaped due to the action of cylindrical lens 19. It is this vibration-induced phase modulation that is used to make the time-of-flight determination interferometrically. Acoustic generation beam 15 is time delayed by optical delay line 22 under computer (not shown) control relative to signal beam 18 in order to record the acoustic response of thin film specimen 25 at different points in time. This type of delay is sometimes referred to as delaying the event instead of delaying the observation. Cylindrical lens 29 is used to collect modulated signal beam 18a and collapse it into photorefractive crystal 28.

Optical interference between incoming modulated signal beam 18a and reference beam 20 in photorefractive crystal 28 leads to the generation of diffracted signal beam 18c that co-propagates with transmitted signal beam 18d as they move to linear photodiode array 31. As shown approximately in FIG. 1, linear photodiode array 31 is positioned at the focal plane of cylindrical lens 30. Adaptation and holographic replication optical phase of modulated signal beam 18b is achieved from photorefractive two-wave mixing. This process is well known and documented and described herein by the following five part model:

a. optical interference inside photorefractive crystal 28 creates spatial, periodic distribution of bright and dark planes of light (interference fringes) on a local level;

b. a redistribution of electrons within photorefractive crystal 28, away from the bright areas and collecting in the dark areas;

c. the local electric field is modulated spatially according to the redistribution of electronic charge and is 90 degrees out of phase with the distribution of electrons;

d. Pockel's effect occurs locally, that is, modulation of the local refractive index of the medium;

e. Reference beam 20 light encountering this spatial periodic refractive index modulation is scattered preferentially into the direction of modulated signal beam 18b creating a holographic duplicate of modulated signal beam 18b.

In addition, the quadrature (the temporal phase difference between diffracted signal beam 18b and transmitted signal beam 18c) of the present invention can be controlled using, for example, an applied electric field (although other methods could be used as well). When applying an electric field, the level of precision dc voltage source 32 normally ranges between approximately 1 kV and 5 kV, depending on the size of photorefractive crystal 28, and is adjusted to obtain the maximum signal at linear photodiode array 31. Optical delay line 27 is used to adjust the delay in reference beam 20 so that reference beam 20 overlaps modulated signal beam 18a. The delay introduced by optical delay line 27 is manually adjusted and fixed.

Cylindrical lens 30 collects and re-focuses diffracted signal beam 18b and transmitted signal beam 18c traveling toward linear photodiode array 31 such that each element of linear photodiode array 31 corresponds to a line position of thin film specimen 25. Interference between incoming diffracted signal beam 18b and transmitted signal beam 18c occurs at linear photodiode array 31, which is at the focal plane of cylindrical lens 30. This interference converts phase modulation into intensity modulation due to ultrafast acoustic perturbation at the surface of thin film specimen 25. Linear photodiode array 31 converts this intensity modulation into voltage modulation for later analysis.

Since the time-of-flight for picosecond acoustics phenomenon is faster than the fastest electronics, normal ultrafast experiments are conducted in a DC manner. This is done by essentially integrating the recorded voltage response over a specified observation time, perhaps 1 second, using a lock-in amplifier. Unfortunately, the recorded response is only good for one point in time when the signal is integrated in this manner. The present invention allows investigation of different times during the acoustic wave propagation in thin film specimen 25 through optically delaying acoustic generation beam 15 with optical delay line 22. Optical delay line 22 employs mirrors and a motion controlled stage.

At different times during the acoustic wave propagation in thin film specimen 25, the acoustic response can be investigated by changing the time delay of acoustic generation beam 15 using optical delay line 22. The entire acoustic response of thin film specimen 16 then can obtained by sweeping optical delay line 22 and recording the voltage response for each point or time. For example, a 0.1 meter optical delay corresponds to an acoustic path of 2 microns in aluminum, assuming a sound velocity of 5 kilometers per second in aluminum.

It is to be understood that it is not possible to investigate the entire acoustic response of thin film specimen 25 in one shot because of the ultrahigh frequency information contained in diffracted signal beam 18b. This is a well known problem, and one that limits the performance of the conventional reflection-based sensing approaches as well. However, the line sensing approach of the present invention is a significant improvement over the point sensing approaches of the prior art because more points along the line are sensed simultaneously in the same amount of time it takes to sense a single point.

It will be understood by those with skill in this art that the length and width of the optical beams used in the practice of this invention can be adjusted as desired by the use of collimating lens. These lens were omitted from FIG. 1 for the sake of clarity.

Figure 2A:
FIGS. 2A and 2B are qualitative representations of the improvement gained through use of the present invention over prior art measurement systems.
Figure 2B:

Reference should now be directed to FIGS. 2A, and 2B, where a comparison between the effects of prior art techniques and of the technique of the present invention is illustrated. In FIGS. 2A and 2B, the dashed lines represent an optical reference wavefront and the solid lines represent a transmitted wavefront. FIG. 2A illustrates how in prior art methods a plane wavefront is used as an interference reference at a photodetector. FIG. 2B shows how the present invention utilizes a phase-duplicate of the original wavefront. In this technique, sensitivity to vibration is optimized since it is the phase difference across photorefractive crystal 28 (FIG. 1) that determines the performance and sensitivity of the interferometer of the present invention. The adaptive wave mixing phase-duplication removes the adverse effects of tilt (linearly varying phase), allowing the interferometer to operate in an automatic manner without manual tuning.

Reference should now be returned to FIG. 1. It is well documented that adaptive optical techniques, such as photorefractive wave mixing, can compensate for spatial and low frequency temporal random phase noise in the detection of the modulation/perturbation of interest in signal beam 18a. This compensation is accomplished in the present invention by exactly duplicating the optical wavefront of modulated signal beam 18a, and creating another unique diffracted signal beam 18b. When the modulated signal beam 18a is interfered with pump beam 11a in photorefractive crystal 28, an electronic holographic grating is created that scatters light from pump beam 11a creating the duplicate signal, diffracted signal beam 18b. This holographic duplication is dynamic both spatially and temporally with a response time dependent on the material of photorefractive crystal 28. This means that it is not important to the sensing process whether or not the optical phase reflected from the top layer 25a of thin film specimen 25 is uniform, the sensitivity is maintained. Conditions that might affect the thin film specimen 25, such as tilting, non-uniformity (non-smooth) of top layer 25a, and ambient vibration, are compensated for in the present invention. This compensation property is a well-known advantage demonstrated in previous literature for photorefractive-based optical sensing of acoustic waves.

Upon exiting photorefractive crystal 28, the diffracted signal beam 18b and transmitted signal beam 18c interfere at linear photodiode array 31. Most importantly, this linear image interference allows sensing along a line corresponding to the line projected onto top layer 25a of thin film specimen 25. This is not possible with conventionally applied interferometers unless manual adjustments are made continuously during a surface inspection. In addition, the photorefractive adaptation of the present invention eliminates the need for quadrature adjustment or control typically associated with prior art measurement procedures when a voltage is applied to PRC 28.

The foregoing description of the embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A line sensing device for laser acoustic inspection of thin film specimens comprising:
   a laser emitting pulses of light;
   a first beamsplitter outputting a first portion of said pulses of light and a second portion of said pulses of light;
   a second beamsplitter receiving said second portion of said pulses of light and outputting a third portion of said pulses of light and a fourth portion of said pulses of light;
   a first optical delay line receiving said first portion of said pulses of light for introducing a predetermined time delay into said first portion of said pulses of light;
   a first cylindrical lens receiving said delayed first portion of said pulses of light and directing said delayed first portion of said pulses of light onto a thin film specimen along a line;
   a second cylindrical lens receiving said third portion of said pulses of light for directing said third portion of said pulses of light onto a thin film specimen so that said third portion of said pulses of light contact said thin film specimen along said line;
   a second optical delay line receiving said fourth portion of said pulses of light for introducing a predetermined time delay into said fourth portion of said pulses of light;
   a third cylindrical lens receiving said delayed fourth portion of said pulses of light and directing said delayed fourth portion of said pulses of light to a photorefractive crystal;
   a fourth cylindrical lens receiving reflected pulses of light from said thin film specimen and directing said reflected pulses of light to said photorefractive crystal;
   a fifth cylindrical lens collecting light from said photorefractive crystal and transmitting said collected light from said photorefractive crystal to a linear photodiode array allowing inspection of said thin film specimens along a line.

2. The apparatus as described in claim 1, wherein said laser emits pulses of light having a duration of approximately 150 femtoseconds and a repetition rate of up to 80 Megahertz.

3. The apparatus as described in claim 1, wherein said laser is a femtosecond laser.

4. The apparatus as described in claim 3, wherein said femtosecond laser is a titanium/sapphire femtosecond laser.

5. A method of sensing a line along a thin film specimen comprising the steps of:
   emitting femtosecond laser pulses;
   splitting said femtosecond laser pulses into a first portion, a second portion, a third portion and a fourth portion of said femtosecond laser pulses;

delaying said first portion of said femtosecond laser pulses by a first predetermined period of time;

directing said delayed first portion of said femtosecond laser pulses at said thin film specimen along a line;

delaying said fourth portion of said femtosecond laser pulses by a second predetermined period of time;

directing said delayed fourth portion of said femtosecond laser pulses to a photorefractive crystal;

collecting pulses of light reflected from said thin film specimen and directing said reflected pulses of light to said photorefractive crystal; and collecting light from said photorefractive crystal and transmitting said collected light to a linear photodiode array allowing inspection of said thin film specimen along a line.

* * * * *